United States Patent [19]

Krueger et al.

[11] Patent Number: 5,153,175
[45] Date of Patent: Oct. 6, 1992

[54] METHOD OF INDUCING SLEEP WITH GHRH COMPLEMENTARY PEPTIDE COMPOSITIONS

[75] Inventors: James M. Krueger; Ferenc Obal, Jr., both of Germantown, Tenn.; Clark E. Grosvenor; Balint Kacsoh, both of State College, Pa.

[73] Assignee: University of Tennesee Research Corporation, Knoxville, Tenn.

[21] Appl. No.: 358,002

[22] Filed: May 25, 1989

[51] Int. Cl.$^5$ .................. A61K 37/02; C07K 7/08; C07K 7/10
[52] U.S. Cl. .......................... 514/12; 514/14
[58] Field of Search .................. 514/14, 12

[56] References Cited

U.S. PATENT DOCUMENTS 4,410,513 10/1983 Momany.
4,411,890 10/1983 Momany.
4,517,181 5/1985 Ling et al.
4,563,352 1/1986 Rivier et al.
4,585,756 4/1986 Brazeau, Jr. et al.
4,833,166 5/1989 Grosvenor et al. .................. 514/14

OTHER PUBLICATIONS

Bohlen et al., *Biochem. Biophys. Res. Comm.* 125: 1005-1012, 1984.
Mayo et al., *Nature* 314: 464-467, 1985.
Baird et al., *Neuroendocrinology* 42: 273-276, 1986.
Ling et al., *Biochem. Biophy. Res. Comm.* 123: 854-861, 1984.
Biro, *Medical Hypotheses*, 7: 969-1007, 1981.
Kaiser and Kezdy, *Science*, 223: 249-255, 1984.
Blalock and Smith, *Biochem. Biophy. Res. Comm.* 121: 203-207, 1984.
Bost et al., *Proc. Natl. Acad. Sci.* 82: 1372-1375, 1985a.
Bost et al., *Biochem. Biophy. Res. Comm.* 128: 1373-1380, 1985b.
Blalock and Bost, *Biochem. J.* 234: 679-683, 1986.
Bost and Blalock, *Molec. Cell. Endocrinol.* 44: 1-9, 1986.
Enright et al., *J. Dairy Sci.* 69: 344-352, 1986.

*Primary Examiner*—Lester L. Lee
*Attorney, Agent, or Firm*—George W. Neuner; Linda M. Buckley

[57] ABSTRACT

The present invention provides a method of inducing sleep in a host which includes administering to the host synthetic peptides, as well as fragments and analogs thereof, complementary to growth hormone releasing hormone.

2 Claims, 4 Drawing Sheets

FIG. 1A

| | | | | | | | | | | |
|---|---|---|---|---|---|---|---|---|---|---|
| GHRH (N-t) | His | Ala | Asp | Ala | Ile | Phe | Thr | Ser | Ser | Tyr |
| +RNA (5') | CAU | GCA | GAC | GCC | AUC | UUC | ACC | AGC | AGC | UAC |
| −RNA (3') | GUA | CGU | CUG | CGG | UAG | AAG | UGG | UCG | UCG | AUG |
| 3'+5' CP (N-t) | Val | Arg | Leu | Arg | STOP | Lys | Trp | Ser | Ser | Met |
| 5'+3' CP (C-t) | Met | Cys | Val | Gly | Asp | Glu | Gly | Ala | Ala | Val |
| GHRH | Arg | Arg | Ile | Leu | Gly | Gln | Leu | Tyr | Ala | Arg |
| +RNA | CGG | AGA | AUC | CUG | GGC | CAA | UUA | UAU | GCC | CGC |
| −RNA | GCC | UCU | UAG | GAC | CCG | GUU | AAU | AUA | CGG | GCG |
| 3'+5' CP | Ala | Ser | STOP | Asp | Pro | Val | Asn | Ile | Arg | Ala |
| 5'+3' CP | Pro | Ser | Asp | Gln | Ala | Leu | STOP | Ile | Gly | Ala |
| GHRH | Lys | Leu | Leu | His | Glu | Ile | Met | Asn | Ser | Gln |
| +RNA | AAA | CUG | CUG | CAC | GAA | AUC | AUG | AAC | AGC | CAG |
| −RNA | UUU | GAC | GAC | GUG | CUU | UAG | UAC | UUG | UCC | GUC |
| 3'+5' CP | Phe | Asp | Asp | Val | Leu | STOP | Tyr | Leu | Ser | Val |
| 5'+3' CP | Phe | Gln | Gln | Val | Phe | Asp | Met | Leu | Pro | Leu |
| GHRH | Gln | Gly | Glu | Arg | Asn | Glu | Gln | Gln | Arg | Ser |
| +RNA | CAA | GGG | GAG | AGG | AAC | GAA | CAG | CAG | AGA | AGA |
| −RNA | GUU | CCC | CUC | UCC | UUG | CUU | GUC | GUC | UCU | UCU |
| 3'+5' CP | Val | Pro | Leu | Ser | Leu | Leu | Val | Val | Ser | Ser |
| 5'+3' CP | Leu | Pro | Leu | Pro | Leu | Leu | Leu | Leu | Leu | Gly |
| GHRM | Arg | Phe | Asn | (C-t) | | | | | | |
| +RNA | AGG | UUC | AAC | 3' | | | | | | |
| −RNA | UCC | AAG | UUG | 5' | | | | | | |
| 3'+5' CP | Ser | Lys | Leu | C-t | | | | | | |
| 5'+3' CP | Pro | Glu | Val | N-t | | | | | | |

| | Hydrophobic | | Hydrophilic | | Hydrophobic | |
|---|---|---|---|---|---|---|
| hGHRH | 22-Leu | 23-Leu | 24-Gln | 25-Asp | 26-Ile | 27-Met |
| rat GHRH | 22-Leu | 23-Leu | 24-His | 25-Glu | 26-Ile | 27-Met |
| 3'-5' CP | 20-Ala | 21-Phe | 22-Asp | 23-Asp | 24-Val | 25-Leu |
| 5'-3' CP | 24-Ala | 23-Phe | 22-Gln | 21-Gln | 20-Val | 19-Phe |

METHOD OF INDUCING SLEEP WITH GHRH COMPLEMENTARY PEPTIDE COMPOSITIONS

This invention was made with Government support under grants HD-20074 HD-04358 and NS-25378-03, awarded by the National Institutes of Health, and N00014-85-K-0773, awarded by the Office of Naval Research. The Government has certain rights in this invention.

BACKGROUND OF THE INVENTION

This invention relates to a method of inducing sleep in a host which comprises administering synthetic Growth Hormone Releasing Hormone complementary peptides to the host.

Growth Hormone Releasing Hormone (GHRH), also known as Growth Hormone Releasing Factor, is a hypothalamic peptide which positively regulates the synthesis and secretion of growth hormone in the anterior pituitary. GHRH was originally isolated and structurally characterized from human pancreatic tumors that caused acromegaly. Since then, GHRH has been isolated from several different species, including rat, pig, cow, man, sheep, and goat (Bohlen et al., *Biochem Biophys. Res. Comm.* 125: 1005–1012, 1984).

Both the function and nature of GHRH have been widely studied.

The amino acid sequence of rat hypothalamic GHRH has been determined (Bohlen et al., 1984, supra). Also, the cDNA to rat GHRH has been reported (Mayo et al., *Nature* 314: 464–467, 1985). Human GHRH is reported to have high homology with rat GHRH and a GH-stimulating effect on the rat pituitary gland (Baird et al., *Neuroendocrinology* 42: 273–276, 1986). Ling et al., Biochem. Biophys. Res. Comm. 123: 854–861, (1984) tested the capacity of a series of C-terminal deleted analogs of synthetic human GHRH to release growth hormone and report that the minimal biologically important core of GHRH with full intrinsic activity comprises the fragment (3–21).

Biro suggested (Biro, *Medical Hypotheses* 7:969–1007, 1981) that protein-protein interactions are based on binding of restricted portions of the proteins that are primarily formed by "informational complementary (ic)" amino acids. He also suggested that these specific complementary amino acids are encoded by complementary DNA sequences; further, interaction between complementary amino acid sequences would occur both in parallel and in antiparallel alignment of the peptides. Although Biro (1981) investigated only the 5'-3' direction, his data also support the significance of the 3'-5' direction by emphasizing the importance of palindrome nucleic acid sequences in encoding the specifically interacting peptide sequences.

Model peptides designed to have minimal homology to the naturally occurring peptide but having the same hydropathic pattern have been demonstrated to exhibit biological activity (See, e.g., Kaiser and Kezdy, *Science*, 223: 249–255, 1984). Blalock and Smith reported that codons for hydrophilic and hydrophobic amino acids on one strand of DNA are complemented by codons for hydrophobic and hydrophilic amino acids on the other DNA strand, respectively, and that codons for slightly hydrophilic ("uncharged") amino acids are complemented by codons for amino acids of the same character (*Biochem. Biophys. Res Comm.* 121: 203–207, 1984). These workers theorize that the two complementary strands of the DNA encode two peptides having hydropathic anti-complementarity. It has been reported that the hydropathic anti-complementarity of a number of amino acids (and hence that of the peptides) based on the genetic code occurs when complementary codons are read in the 5'-3' as well as in the 3'-5' direction (Bost et al., *Proc. Natl. Acad. Sci.* 82: 1372.1375, 1985a., Bost et al., *Biochem. Biophys. Res. Comm.* 128: 1372–1380, 1985b; Blalock and Bost, *Biochem. J.* 234: 679–683, 1986).

Bost et al., 1985a, supra, have reported that a peptide ("HTCA") corresponding to the complementary (5'-3') RNA sequence of ACTH (1–24) mRNA is capable of binding synthetic ACTH as determined by ELISA. Blalock and Bost, supra, have reported that both 3'-5' and 5'-3'complementary peptides bind $^{125}$I-ACTH in a solid-phase binding assay. Similar binding was reported for 5'-3' complementary peptides of γ-endorphin (Bost et al., 1985a, supra). Antibodies raised against the complementary peptide, HTCA, have been reported to stimulate corticosterone secretion of adrenocortical cells in vitro (Bost et al., 1985a, supra). It is also reported that, using the same antibodies in immune affinity chromatography, the ACTH-receptor was purified and its molecular structure and $^{125}$I-ACTH binding characteristics were determined (Bost and Blalock, *Molec. Cell. Endocrinol.* 44: 1–9, 1986). According to Bost et al., 1985b, supra, messenger RNA sequences complementary to the mRNA sequences for the receptors of epidermal growth factor (EGF), interleukin-2 (IL-2) and transferrin (TF) encode peptides having high homologies with the amino acid sequence of their respective ligands, if the transcription is carried out in 3'-5' direction. Gorcs et al., Peptides, 7: 1137–1145 (1986) report possible recognition the GnRH receptor by an antiserum against a peptide encoded by nucleotide sequence complementary to mRNA of a GnRH precursor peptide.

GHRH peptides have been reported to have applications in the fields of animal husbandry, clinical medicine and basic research For example, it was determined that administration of human GHRH to lactating holstein cows increases the secretion of growth hormone consistently and causes an apparent increase in feed to milk conversion (Enright et al., *J. Dairy Sci.* 69: 344–351, 1986). GHRH peptides are useful in vitro e.g., as unique research tools for understanding how growth hormone secretion is regulated at the pituitary level and are also be useful in vivo, e.g., to treat symptoms related to growth hormone deficiencies to increase the rate and extent of growth in commercial animals, to increase milk yield in commercial animals.

SUMMARY OF THE INVENTION

The present invention provides a method of inducing sleep by use of biologically important synthetic peptides complementary to GHRH, and fragments and analogs thereof.

One method of inducing sleep in a host in accordance with the present invention comprises the step of administering to a host a predetermined quantity of a composition comprising an effective amount of a synthetic peptide having the formula:

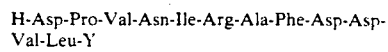

H-Asp-Pro-Val-Asn-Ile-Arg-Ala-Phe-Asp-Asp-Val-Leu-Y wherein Y is OH or NH₂ or a non-toxic salt thereof, in combination with a pharmacologically acceptable carrier therefor. This peptide is complementary in the 3'-5' direction to residues 14-25 of GHRH and is hereinafter referred to as 3'-5' peptide.

Another method of inducing sleep in accordance with the present invention comprises the step of administering to a host a predetermined quantity of a composition comprising an effective amount of a synthetic peptide having the formula:

H-Val-Glu-Pro-Gly-Ser-Leu-Phe-Leu-Val-Pro-Leu-
Pro-Leu-Leu-Pro-Val-His-Asp-Phe-Val-Gln-Gln-
Phe-Ala-Gly-Ile-Y wherein Y is OH or NH₂ or a non-toxic salt thereof in combination with a pharmacologically acceptable carrier therefor. This peptide is complementary in the 5'-3 direction to residues 18-43 of GHRH (hereinafter referred to as 5'-3' CP).

Fragments and analogs of the 3'-5' and 5'-3' peptides are also useful in the practice of the claimed invention.

Thus, the GHRH complementary peptide for use in the present invention as well as fragments and analogs thereof, may be administered in vivo to hosts, to induce sleep.

BRIEF DESCRIPTION OF THE DRAWINGS

FIG. 1a illustrates the RNA sequence and amino acid sequence of the 3'-5' and 5'-3' CP.

FIG. 1b illustrates the homology of the 3'-5' and 5'-3' CP in the region that corresponds to GHRH (22-27).

DETAILED DESCRIPTION OF THE INVENTION

Figure 2A:
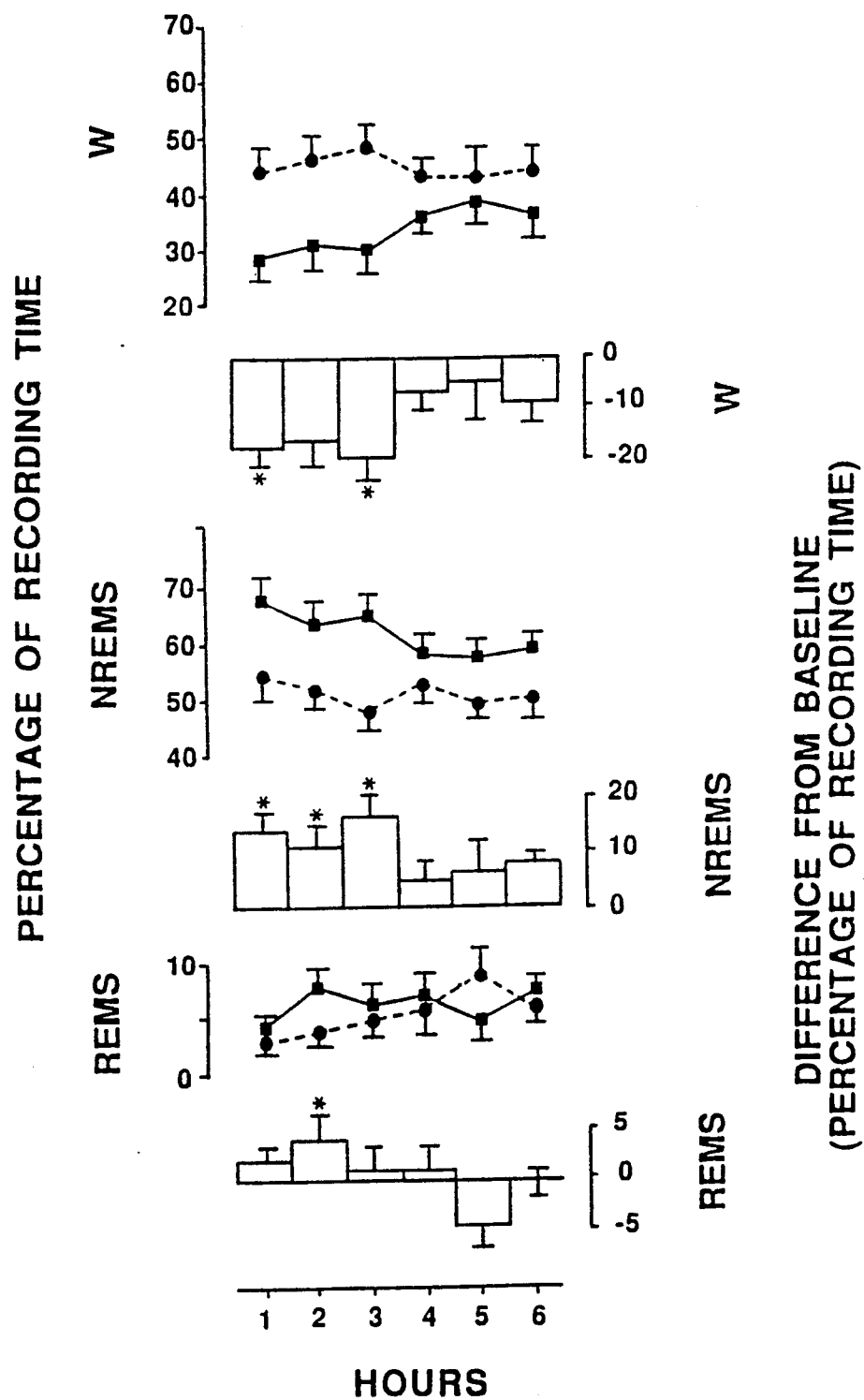
FIG. 2 illustrates the effect of the 3'-5' and 5'-3' CP in inducing sleep.

The methods of the present invention use complementary peptides overlapping the sequence of human GHRH (18-25). As mentioned above, Ling et al. found a gradual decrease in relative GH-releasing potency of C-terminal deleted GHRH fragments until reaching hGHRH (1-27) (12% relative potency). A sharp decrease in biological activity was found with shorter fragments, e.g., hGHRH (1-24): 0.02% relative potency; hGHRH (1-19): No activity. The amino acid sequence of the 5'-3' CP was derived from the mRNA (Mayo et al., supra) for rat GHRH.

Both the 3'-5' and 5'-3' CP contain a 6 amino acid-long sequence that is identical with a sequence in rat GHRH and human GHRH in hydropathic nature (See FIG. 1b). If one aligns the amino acid sequences of the 3'-5' and 5'-3' CP in antiparallel direction one can find a high homology in their amino acid distribution in the region that corresponds to GHRH (22-27) (FIG. 1b). The hydrophobic amino acids are the same in both the 3'-5' and 5'-3' CP, while the hydrophilic ones are closely related but have a different charge (Asp vs. Gln). On the contrary, other peptides in the glucagon family have "uncharged" amino acids in position 25 (Trp in gastric inhibitory peptide and glucagon, Gly in secretin, Ser in vasoactive intestinal peptide [VIP]and peptide histidine-isoleucine-27 [PHI-27]) and in position 22 (Tyr in VIP and PHI-27).

It is well known to those skilled in the art that certain fragments of an analogs of peptides will retain their biological activity. In fact, it has been reported that analogs and fragments of other sleep promoting peptides are also somnogenic. Thus, it is expected that fragments and analogs of both the 3'-5' CP and the 5'-3' CP will be useful in the practice of the present invention.

It is expected that the substitution of D amino acid for L amino acids in both the 3'-5' CP and 5'-3' CP would result in a peptide having a sleep-promoting action, for example. L-ala could be replace by D-ala in both the 3'-5' CP and 5'-3' CP, or L-tyr could be replaced by D-tyr in the 3'-5' CP. Such changes are often useful to reduce the rate of peptide breakdown, thereby reducing the amount needed for an effective somnogenic dose. By way of example, it has been reported that similar changes were made in the nonapeptide DSIP, and that it retained its somnogenic activity. See, e.g., Kovalzon, V. et al. *Sleep* 86. pp 172-184, ed. by Koella, W.P. et al., Gustav Fischer Verlag. Stuttgart, N.Y. 1988., and Obal F. et al. *Pharmacol. Biochem. Behav.* 24: 889-894 (1986).

It is also expected that phosphorylation of certain amino acid residues in both the 3'-5' and 5'-3' CP would result in sleep-promoting peptides. For example, if the ser residue of either the 5'-3' CP or the 3'-5' CP were phosphorylated, it is anticipated that such analogs will be somnogenic. By way of example, phosphorylation of the ser residue of DSIP results in a molecule that retains its ability to induce sleep (Oral Communication by S. Inoue, (Tokyo) at the Endogenous Sleep Factors Seminar, Nov. 11, 1988, Honolulu, Hi.).

It is well known that fragments of peptides may retain the biological activity of the peptide. It is expected that removal of one or more amino acids from or addition of one or more amino acids to the amino terminal or carboxyl terminal of either the 5'-3' or the 3'-5' CP would result in somnogenic fragments. For example, the removal of val from the 5'-3' CP would most likely not alter biological activity. By parallel example, the fragment produced by removal of 3 amino acids from the carboxyl terminal of DSIP, has been reported to be biologically active (ref. 2, Obal et al. supra). Similarly, if amino acids are added to the carboxyl terminal of another somnogenic peptide, N-acetyl muramyl-L-alanyl-D-isoglutamine, to form, for example, N-acetyl-muramyl-L-alanyl-D-isoglutamyl-L-diaminopimelyl alanine, somnogenic activity is retained. (See, e.g., Krueger, J.M. et al., *Brain Res.* 403:249-257 (1987).

Thus, selection of somnogenic analogs and fragments of the 3'-5' and 5'-3' CPs of the present invention can be accomplished by those skilled in the art without undue experimentation.

The peptides for use in the present invention can be synthesized by any suitable method, such as by exclusively solid-phase techniques, by partial solid-phase techniques, by fragment condensation, by classical solution couplings, or by the employment of recently developed recombinant DNA techniques.

The 12 amino acid long 3'-5' CP of GHRH and the 26 amino acid long 5'-3' CP of GHRH (See FIG. 1a) were synthesized at the Molecular Resource Center, Macromolecular Synthesis Laboratory, University of Tennessee, Memphis, Dr. T. C. Cooper, Director. Applied Biosystems Model 430A, a fully automatic instrument-reagent system for solid phase peptide synthesis, was used. The Model 430A utilized an optimized system based on R. B. Merrifield's concept of solid phase peptide synthesis (Virender et al., *Anal. Biochem.*, 117: 147-157, 1981). Typically, solid phase synthesis occurs from the 'C-' to the 'N-terminal' of the peptide sequence. The alpha-carboxyl group of the C-terminal amino acid residue is covalently attached to an insoluble polystyrene resin bead through an organic linker. The alpha-amino group of this amino acid, and all the other amino acids used in synthesis are protected by an organic moiety.

A general synthesis cycle consists of: deprotection of the resin-bound alpha-amino group, then washing, neutralization and washing of the resin. Next in the cycle is the formation of a peptide bond between the deprotected alpha-amino group and the activated carboxyl of the next alpha-amino protected amino acid of the sequence. This cycle is repeated until the desired sequence is complete. When synthesis is complete, the peptide is deprotected and cleaved from its polymer support; it is then separated from the resin and purified.

The 3'-5' CP and 5'-3' CP, fragments thereof, or analogs thereof having well known substitutions and/or additions, as well as non-toxic salts of any of the foregoing, hereinafter collectively referred to as the active ingredient may be prescribed or administered to a host in accordance with the present invention to induce sleep.

The amount of said active ingredient will, of course, depend upon the severity of the condition being treated, the route of administration chosen and the specific activity of the active ingredient, and ultimately will be decided by the attending physician or veterinarian. Such amount of active ingredient as determined by the attending physician or veterinarian is also referred to herein as an "effective" amount. In general, an amount of active ingredient from 0.01 to 1.0 nanomole per kg (body weight) is sufficient to induce slow wave sleep when administered intracerebroventricularly (icv).

The active ingredient may be administered by any route appropriate to the condition being tested, e.g., orally, rectally, intravenously, intramuscularly, intraperitoneally, or intraventricularly. Preferably, the peptide is administered orally to the mammal being treated. It will be readily appreciated by those skilled in the art that the preferred route may vary.

While it is possible for the active ingredient to be administered as the pure or substantially pure compound, it is preferable to present it as a pharmaceutical formulation or preparation.

The formulations for use in the present invention, both for veterinary and for human use, comprise the 3'-5' CP and 5'-3' CP, or fragments or analogs thereof, as described above, together with one or more pharmaceutically acceptable carriers therefor and, optionally, other therapeutic ingredients The carriers must be "acceptable" in the sense of being compatible with the other ingredients of the formulation and not deleterious to the recipient thereof. Such carriers are well known to those skilled in the art of pharmacology. Desirably, the formulation should not include oxidation agents and other substances with which peptides are known to be incompatible. The formulations may conveniently be presented in unit dosage form and may be prepared by any of the methods well known in the art of pharmacy All methods include the step of bringing into association the active ingredient with a carrier which may constitute one or more accessory ingredients In general, the formulations are prepared by uniformly and intimately bringing into association the active ingredient with liquid carriers or finally divided solid carriers or both, and then, if necessary, shaping the product into the desired formulation.

Formulations suitable for parenteral administration conveniently comprise sterile aqueous solutions of the active ingredient, which solutions are preferably isotonic with the blood of the recipient. Such formulations may be conveniently prepared by dissolving solid active ingredient in water to produce an aqueous solution, and rendering said solution sterile. The formulations may be presented in unit or multi-dose containers for example, sealed ampules or vials.

Biological assays for sleep-promoting activity were performed on rabbits provided with chronically implanted ventricular guide tubes and four epidural screw electrodes for EEG. The animals were allowed at least one week to recover from surgery prior to their use for assays. Samples for testing were taken up in sterile artificial cerebrospinal fluid and a total of 50 ml solution was infused intraventricularly (ICV) at the rate of 25 ul/min through a No. 26 hypodermic needle inserted through a guide tube. Following the infusion and removal of the infusion probe the animals were left undisturbed for 6-8 hours while EEG and bodily movements were recorded.

Slow wave sleep (SWS) was scored in two ways: (i) by conventional subjective scoring of the duration of SWS from polygraph records and (ii) by digital printout of integrated mean rectified cortical slow waves ($\frac{1}{2}$-4 Hz), thus obtaining a measure of the amplitude was well as duration of delta wave EEG activity. Control animals were also assayed at the same time.

The results of these assays demonstrate that both the 3'-5' and the 5'-3' CP have the capacity to enhance sleep. Thus, after administration of either of these substances, the recipient animal spent significantly more time in SWS and rapid-eye-movement sleep. Although excess sleep was observed, this sleep appeared normal, in that animals continued to cycle through the various states of vigilance. The temperatures of the animals remained normal. In addition, their behavior was normal in that they could be aroused if they were asleep. They continued to eat, drink and groom during periods of spontaneous awakenings.

The invention will be further understood with reference to the following examples which are purely exemplary in nature and are not meant to be utilized to limit the scope of the invention.

EXAMPLE 1

Synthesis of 3'-5'CP and 5'-3' CP

The syntheses of 3'-5' CP amide, with the sequence:

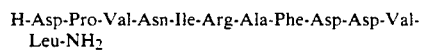
H-Asp-Pro-Val-Asn-Ile-Arg-Ala-Phe-Asp-Asp-Val-Leu-NH$_2$ and the 5'-3' CP amide, with the sequence:

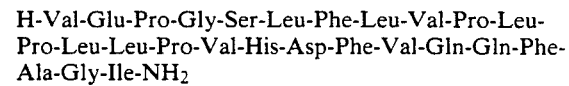
H-Val-Glu-Pro-Gly-Ser-Leu-Phe-Leu-Val-Pro-Leu-Pro-Leu-Leu-Pro-Val-His-Asp-Phe-Val-Gln-Gln-Phe-Ala-Gly-Ile-NH$_2$ were performed on an Applied Biosystems Model 430A Peptide Synthesizer which is totally microprocessor controlled, utilizing software version 1.2. This machine is a solenoid controlled, gas-driven (prepurified nitrogen or argon) synthesizer. The aminomethyl resin was purchased from Applied Biosystems, Inc. and had an amino acid substitution of about 0.6-0.7 millimoles/gm. of resin. This resin consists of 1% cross-linked polystyrene to which had been attached a phenylacetamidomethyl (PAM) group. The carboxyl terminal amino acid, leucine or isoleucine, in these cases, was attached to the PAM resin and contained an amino terminal blocked with the TBOC (t-butoxylcarbonyl)-protecting group.

After deprotection of this group on the machine utilizing trifluroacetic acid, the peptide was built in a stepwise manner. TBOC-protected amino acids were purchased in pre-weighed amounts (approximately 2 mmoles) in sealed cartridges from Applied Biosystems. The chemical forms of the amino acids used in these peptides are listed below:

| | |
|---|---|
| t-BOC-L-Aspartic acid(O-Benzyl) | t-BOC-L-Glutamine |
| t-BOC-L-Asparagine | t-BOC-L-Glutamate (O-BZ) |
| t-BOC-L-Alanine | t-BOC-L-Glycine |
| t-BOC-L-Arginine (Tosyl) | t-BOC-L-Serine (Benzyl) |
| t-BOC-L-Leucine H$_2$O | t-BOC-L-Histidine (Tos) |
| t-BOC-L-Isoleucine | t-BOC-L-Valine |
| t-BOC-L-Phenylalanine | |
| t-BOC-L-Proline | |

O-Benzyl, Benzyl and Tosyl (p-toluenesulfonyl) refer to the type of amino and hydroxyl protecting groups present on the amino acid derivatives.

Briefly, the resin-bound amino acid is deprotected by the addition of trifluroacetic acid, neutralized and washed extensively T-BOC protected amino acids are dissolved in suitable solvents and transferred to the activator vessel of the instrument DCC (Dicyclohexylcarbodiimide) is then added to the dissolved amino acid, and a symmetric anhydride is formed, called a PSA (protected symmetric anhydride). A by-product of the reaction, dicyclohexylurea, forms a precipitate. The equation for this reaction is given below:

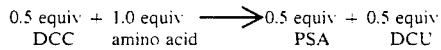

0.5 equiv + 1.0 equiv  →  0.5 equiv + 0.5 equiv
DCC      amino acid       PSA         DCU There are three exceptions to the use of amino acid PSA s in the Model 430A cycles; asparagine, glutamine and arginine are coupled as 1-hydroxybenzotriazole (HOBT) esters. These esters are utilized because symmetric anhydrides of these amino acids are unstable and undergo unacceptable side reactions. In addition to being HOBT-esters, these amino acids are double coupled, that is, two cartridges of these amino acids are required for each cycle. After the initial coupling, the resin is washed, then the coupling is repeated, to increase the yields.

After the PSA is prepared, the amino acid is transferred to the concentrator vessel, where it is purged with nitrogen to remove volatile dichloromethane (DCM). N,N-Dimethylformamide (DMF) is then added to the amino acid. Individual PSA's have varying stabilities in DCM/DMF mixtures, so the temperatures are carefully regulated by the program. HOBT-esters are not purged since they are unstable.

Certain individual amino acids require special treatment. Histidine is one such amino acid. It is purchased as the DCHA (dicyclohexylamine) salt and passed through a suitably prepared AG-50-X8(H$^+$) ion exchange column in DCM just before use. T-BOC-his(-Tos) is unstable in DCM at room temperature, and thus must be placed on the machine within 4 hours of use. Two other alterations in the cycle are required with histidine. Since the amino acid is supplied as a solution, no DCM is delivered to the cartridge, and the purge cycle is shortened to 6.5 minutes because of its instability.

As the amino acids are activated and the solvents are evaporated and changed, the resin is treated with trifluoroacetic acid (TFA) in DCM twice, then washed with DCM to remove some of the TFA. The resin is then neutralized with diisopropylethylamine (DIEA) in DMF and washed with DMF. DMF is the solvent of choice for coupling of activated amino acids to the growing peptide chain.

After the peptide is complete, the T-BOC group is then removed with the standard deprotection step and washed with DCM.

Synopsis of one single cycle

Addition of the first amino acid residue of the first peptide, isoleucine, was carried out in the following manner:

1. The amino acid cartridge was punctured with a needle assembly and approximately 3 ml of dichloromethane (DCM) was delivered to the powdered amino acid. The solution was mixed with nitrogen bubbles for approximately 2 minutes, and the solution transferred to the activator vessel.

2. One millimole of 0.5 M dicyclohexylcarbodiimide (DCC) in dichloromethane was delivered to the activator vessel followed by gas purging to mix. The by-product of this reaction, dicyclohexylurea, begins to precipitate almost immediately. After 8 minutes, the solution is filtered through a glass frit, and delivered to the concentrator vessel.

3. During the activation and concentration cycles, the resin, in the reaction vessel, was treated in the following way:
   a. 33% trifluoroacetic acid (TFA) in DCM for 2.5 minutes
   b. 50% TFA in DCM for 18 minutes
   c. Three DCM washes
   d. 10% DIEA in DMF for 3 minutes
   e. Five DMF washes The deprotection steps are identical to the above for all amino acids.

4. In the concentrator vessel, the DCM solution was purged with nitrogen gas for a total of about 16 minutes, and approximately 4 ml of DMF was added. The temperature was automatically controlled at 15° C. or below After the last DMF wash of the resin, the activated amino acid in DMF was delivered to the reaction vessel and coupled for about 25 minutes with vigorous vortexing. Other amino acids utilizing this coupling time are histidine, leucine, isoleucine, phenylalanine and proline. Others such as aspartic acid, glycine, serine and alanine use about 18 minutes. Arginine and asparagine are coupled twice for 42 minutes each.

5. As the peptide chain lengthens, longer coupling times are required and are automatically incorporated into the compiled program as it progresses.

6. After coupling was completed, the resin was drained and washed five times with DCM. Activation of the next amino acid and deprotection of the resin for the next cycle was begun.

Synopsis of a double couple cycle

1. Two amino acid cartridges were required for the double couple cycles of argining and asparagine. These were placed one after another in the guideway of the Model 430A synthesizer.

2. The first amino acid cartridge was punctured with a needle assembly and approximately 4 ml of HOBT (1-Hydroxybenzotriazole) in N,N-Dimethylformamide (DMF) (2 mmole) was delivered to the cartridge to dissolve the amino acid Asparagine requires the addition of 0.3 ml of DCM, and arginine requires 1.5 ml of DCM for complete dissolution. After mixing (6.5 min for asparagine, 8 minutes for arginineJ), the solution was transferred to the activator vessel.

3. The HOBT-ester double couple cycles all employ the same transfer process. The HOBT/amino acid mixture is added to 4 ml (2 mmoles) of DCC (dicyclohexylcarbodiimide) in the activator vessel. After precipitation of DCU, the HOBT-ester is transferred to the concentrator vessel after being filtered through a glass frit.

4. The solution is then directly transferred to the reaction vessel, without gas purging.

5. During the previously described activation phase, the resin was deprotected using the following schedule:
  a. 33% TFA in DCM for 2.5 minutes
  b. 50% TFA in DCM for 18 minutes
  c. Three DCM washes
  d. Five DMF washes
  f. Begin first coupling periodj 6. Coupling then takes place for about 42 minutes with vigorous vortexing. The resin is then washed according to the following schedule:
  g. Three DMF washes
  h. 10% DIEA in DMF for 45 seconds
  i. One DMF wash
  j. Three DCM washes 7. The second amino acid cartridge is prepared in the same manner as the first, and coupled f r another 42 minutes. The resin is then drained, washed with DMF, then 5 times with DCM.

EXAMPLE 2

Administration of 5'-3' CP and changes in Vigilance

Operation and experimental procedure. Adult male New Zealand White Pasteurella-free rabbits, weighing 3-4 kg, were purchased from Myrtle's Rabbitry (Thompson Station, Tenn.). Under ketamine-xylazine (3.5-5.0 mg/kg iv) anesthesia, animals were provided with chronically implanted EEG electrodes, a glass-bead thermistor, and a cerebral ventricular guide tube (Krueger, J.M et al., *Am. J. Physiol.* 251 (Regulatory Integrative Comp. Physiol. 20): R591-R597, 1986; and Walter J.D. et al., *Am. J. Physiol.*, 250 (Regulatory Integrative Comp. Physiol. 19): R96-R103, 1986). Briefly, stainless steal screws were implanted over the frontal parietal, and occipital cortex; and a small (1 mm diam) 50-k$\Omega$ thermistor (Fenwall Electronics) was placed 3 mm into the parietal cortex. Wires from Amphenol plugs (no. 223-1509) were soldered to the screws for EEG recordings and to the thermistors for brain temperature ($T_{br}$) recordings. The ventricular guide tube was implanted 4 mm lateral to the bregma; during the implantation procedure, pressure at the tip of the infusion needle was monitored and used as an aid to locate the ventricle (See, e.g., Krueger, J.M et al., *Am. J. Physiol.*, 246 (Regulatory Integrative Comp. Physiol. 15): R994-R999, 1984). Dental acrylic (DuzAll) was then used to insulate the leads and to secure the guide tube and EEG/thermistor plugs to the skull. A topical antibiotic (Bacitracin, Lilly) was applied to the incision, and 150,000 U of Duracillin (Lilly) were administered intramuscularly. At least 1 week was allowed for recovery.

Animals were housed in rooms on a 12:12-h light-dark cycle (0600-1800 h light) maintained at 21 ±2° C. The day before an experiment animals were brought to experimental chambers (Hotpack model 352600) for an overnight acclimation period. Each experimental chamber was also kept at 21 ±2° C. on a 12:12-h light-dark cycle. Food and water were available ad libitum at all times. At the top of the recording chamber, BRS/LVE electrical contact swivel was fixed; this allowed the rabbits free movement during recording periods. From the other end of the swivel a cable led to a Grass polygraph model 7D. Before each recording period the rabbits were connected to the recording cable for a 1-h habituation period, but data were not collected during this time.

Rabbits were then briefly taken out of the experimental cages and given the 3'-5' or 5'-3' CP (the "test substance"). [When animals received intracerebroventricular (ICV) injections, appropriate amounts of test substances (0.1-10.0 ul) were diluted to 50 ul with artificial CSF [3 mM KCL, 1.15 mM $CaCl_2$ and 0.96 mM $MgCl_2$ in pyrogen-free saline (PFS), 1.55 mM NaCl (Abbott)]; these solutions were slowly infused over 2 min. Immediately after injection, colonic temperatures ($T_{co}$) were measured using a calibrated thermistor probe (Yellow Springs Instruments) inserted 10 cm into the colon; then the rabbits were returned to the experimental cages for a 6-h recording period. After the recording period $T_{co}$ was measured again. Injection (ICV) took place between 0900 and 1000 h.

EEG, ratios of $\theta/\delta$ cortical EEG activity, $T_{br}$ and motor movement were recorded from animals to define the state of vigilance (see below). Cortical EEG signals were fed into a Buxco (Sharon, Conn.) DL.24 EEG analyzer, and the rectified average voltages in the 0.5- to 3.5-Hz ($\delta$), 4-to 7.5-Hz ($\theta$), 8- to 12.5-Hz ($\alpha$), and 13- to 25-Hz($\beta$) frequency bands were printed on paper each minute. In addition the ratios of $\theta/\delta$ voltages were computed, and these values were continuously recorded simultaneously with the EEG on polygraph paper.

The Grass and Buxco amplifiers, filters and averager were calibrated using sine waves of known peak-to-peak voltage and frequency. To evaluate $T_{br}$ implanted thermistors were calibrated by reference to $T_{co}$; this method assumes that $T_{br}$ follows $T_{co}$ within a constant range. Thus, when an animal received a pyrogenic substance, $T_{co}$ was taken before and after fever developed while $T_{br}$ was simultaneously recorded. The difference between the two $T_{br}$ on the polygraph paper was assumed to be equal to the difference between the two $T_{co}$; this allowed quantitation of $T_{br}$ at other times Rabbit body movements were monitored using a Grass tremor transducer (model SPAI) attached to the recording cable.

Polygraph recordings were analyzed visually to determine periods of W, SWS and rapid-eye-movement (REM) sleep. The recordings were divided into 12-s epochs; each epoch was classified as either W, SWS or REM sleep as follows. W was characterized by low-voltage EEG, high incidence of body movement, mid-level range of $\theta/\delta$ ratios, and a decreasing $T_{br}$ after REM sleep episodes or increasing $T_{br}$ after SWS episodes. SWS was identified by increased EEG slow-wave voltage, little or no body movements, low $\theta/\delta$ ratios, and a decreasing $T_{br}$. REM sleep was identified by a low-voltage EEG, phasic body movements, high $\theta/\delta$ ratios, and a relatively rapid increase in $T_{br}$.

Figure 2B:
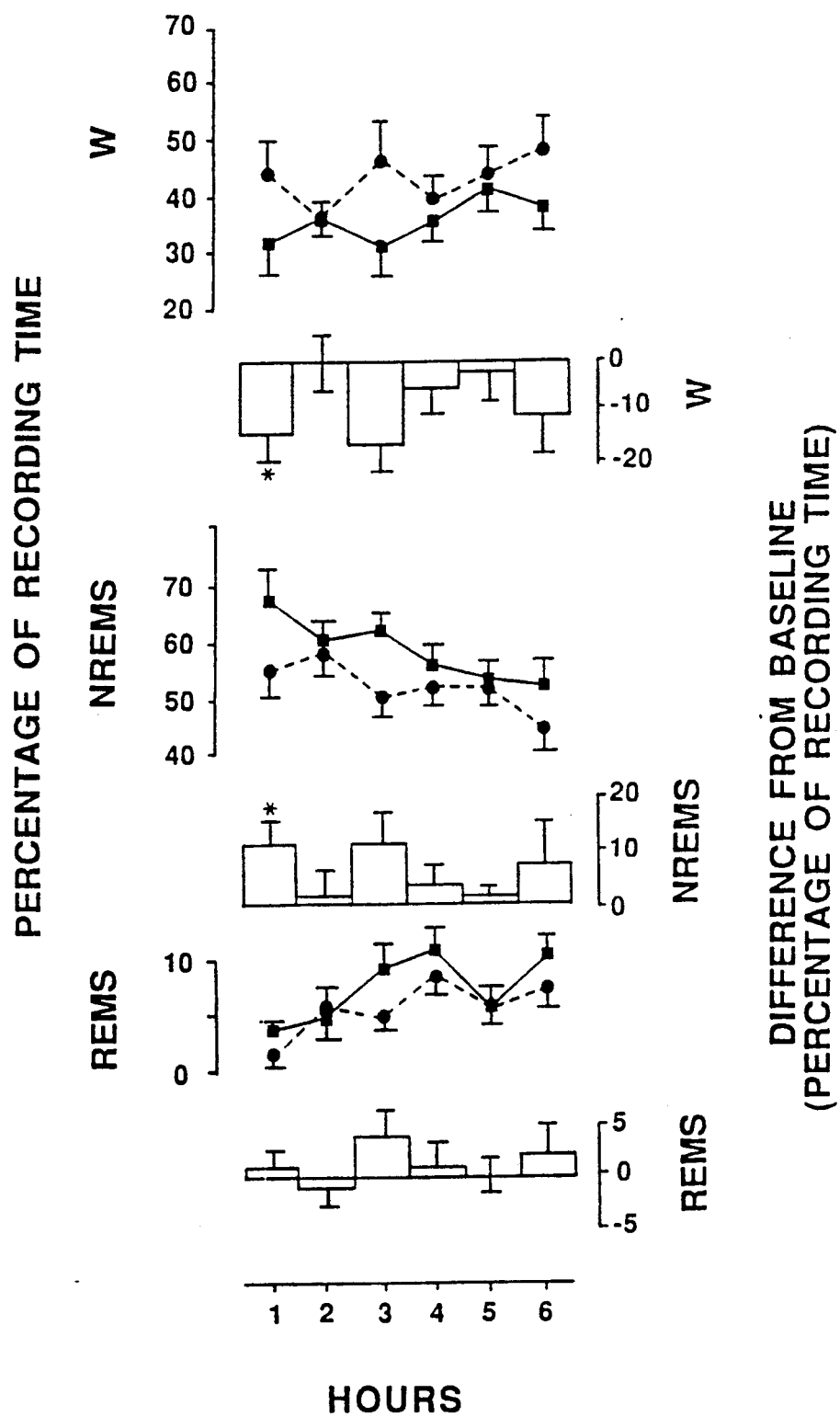

The percentage of time spent in SWS and REM sleep was determined for each hour (FIGS. 1 and 2) and for the total recording period (Tables 1 and 2). Printed average voltage was used to calculate hourly mean voltage in each frequency band; only values for the $\delta$-frequency band are presented (Table 1 and FIG. 1), since values for the other frequency bands were not affected by test substances. In addition, maxium values for $\delta$-wave voltages during SWS episodes were determined after rTNF treatment. These values were obtained by first identifying the 12 maximum 1-min printed average voltages for each rabbit, then checking the polygraph record to make sure these were associated with periods of SWS rather than with movement artifact. The values for each rabbit for both control and experimental conditions were averaged; for different experimental groups the means ± SE of these averages were then determined (Table 1). Student s t tests for paired data were used for comparison between data obtained from the same animals under experimental and control conditions. A significance level of $P<0.05$ was used.

It is understood that the examples and embodiments described herein are for illustrative purposes only, and that various modifications or changes in light thereof that will be suggested to persons skilled in the art are to be included in the spirit and purview of this application and the scope of the approved claims.

What is claimed is:

1. A method of inducing sleep in a host, the method comprising the step of administering to the host an effective quantity of a synthetic peptide having the formula:

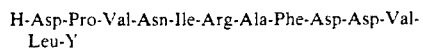

wherein Y is OH or $NH_2$ or a non-toxic salt thereof.

2. A method of inducing sleep in a host, the method comprising the steps of administering to the host an effective quantity of a composition comprising an effective amount of a synthetic peptide having the formula:

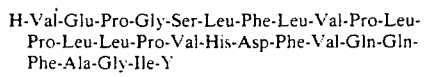

wherein Y is OH or $NH_2$ or a non-toxic salt thereof, in combination with a pharmacologically acceptable carrier therefor.

* * * * *